United States Patent
Bettuchi et al.

(10) Patent No.: US 8,210,414 B2
(45) Date of Patent: Jul. 3, 2012

(54) STAPLE BUTTRESS RETENTION SYSTEM

(75) Inventors: Michael Bettuchi, Middletown, CT (US); Brian Nentwick, Greenfield Center, NY (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/205,937

(22) Filed: Aug. 9, 2011

(65) Prior Publication Data

US 2011/0290852 A1    Dec. 1, 2011

Related U.S. Application Data

(63) Continuation of application No. 12/984,891, filed on Jan. 5, 2001, now Pat. No. 8,016,177, which is a continuation of application No. 11/807,144, filed on May 25, 2007, now Pat. No. 8,038,045.

(51) Int. Cl.
*A61B 17/068* (2006.01)

(52) U.S. Cl. ............... 227/176.1; 227/175.1; 227/181.1; 227/19; 606/151; 606/142; 606/219

(58) Field of Classification Search ............... 227/175.1, 227/176.1, 181.1, 19; 606/151, 142, 219
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A | 4/1993 | Brinkerhoff et al. | |
| 5,263,629 A | 11/1993 | Trumbull et al. | |
| 5,314,471 A | 5/1994 | Brauker et al. | |
| 5,344,454 A | 9/1994 | Clarke et al. | |
| 5,392,979 A | 2/1995 | Green et al. | |

(Continued)

FOREIGN PATENT DOCUMENTS

DE    199 24 311 A1    11/2000

(Continued)

OTHER PUBLICATIONS

European Search Report EP 06016962.0 dated Jan. 3, 2007.

(Continued)

*Primary Examiner* — Brian D Nash
*Assistant Examiner* — Michelle Lopez

(57) ABSTRACT

A surgical stapling instrument is provided having systems for securing buttress material to the anvil and staple containing cartridge associated with the surgical instrument. The system includes a retainer configured to engage the anvil or the staple containing cartridge and capture the buttress material between the retainer and the anvil or staple containing cartridge. The disclose retainer engages the anvil or staple containing cartridge in snap fit or friction fit fashion. The buttress material includes a circumferential perforation line enabling the center of the buttress material to be stapled to tissue while the remainder of the buttress material remains with the anvil or staple containing cartridge.

26 Claims, 10 Drawing Sheets

U.S. PATENT DOCUMENTS

| | | | |
|---|---|---|---|
| 5,397,324 A * | 3/1995 | Carroll et al. | 606/139 |
| 5,425,745 A | 6/1995 | Green et al. | |
| 5,441,193 A * | 8/1995 | Gravener | 227/176.1 |
| 5,441,507 A | 8/1995 | Wilk et al. | |
| 5,468,253 A | 11/1995 | Bezwada et al. | |
| 5,503,638 A | 4/1996 | Cooper et al. | |
| 5,542,594 A * | 8/1996 | McKean et al. | 227/178.1 |
| 5,549,628 A | 8/1996 | Cooper et al. | |
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,895,412 A | 4/1999 | Tucker | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov et al. | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,685,714 B2 | 2/2004 | Rousseau | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,927,315 B1 | 8/2005 | Heinecke et al. | |
| 7,128,748 B2 | 10/2006 | Mooradian et al. | |
| 7,147,138 B2 * | 12/2006 | Shelton, IV | 227/176.1 |
| 7,434,717 B2 | 10/2008 | Shelton, IV et al. | |
| 7,438,209 B1 | 10/2008 | Hess et al. | |
| 7,547,312 B2 * | 6/2009 | Bauman et al. | 606/151 |
| 7,559,937 B2 | 7/2009 | de la Torre et al. | |
| 7,604,151 B2 | 10/2009 | Hess et al. | |
| 7,665,646 B2 | 2/2010 | Prommersberger | |
| 7,669,747 B2 | 3/2010 | Weisenburgh, II et al. | |
| 7,744,627 B2 | 6/2010 | Orban, III et al. | |
| 7,793,813 B2 | 9/2010 | Bettuchi | |
| 7,823,592 B2 | 11/2010 | Bettuchi et al. | |
| 7,845,533 B2 | 12/2010 | Marczyk et al. | |
| 7,845,536 B2 | 12/2010 | Viola et al. | |
| 7,909,224 B2 | 3/2011 | Prommersberger | |
| 2002/0016626 A1 | 2/2002 | DiMatteo et al. | |
| 2002/0019187 A1 | 2/2002 | Carroll et al. | |
| 2002/0052622 A1 | 5/2002 | Rousseau | |
| 2002/0091397 A1 | 7/2002 | Chen | |
| 2002/0133236 A1 | 9/2002 | Rousseau | |
| 2002/0138152 A1 | 9/2002 | Francis et al. | |
| 2002/0151911 A1 | 10/2002 | Gabbay | |
| 2002/0165559 A1 | 11/2002 | Grant et al. | |
| 2002/0165562 A1 | 11/2002 | Grant et al. | |
| 2002/0165563 A1 * | 11/2002 | Grant et al. | 606/151 |
| 2002/0177859 A1 | 11/2002 | Monassevitch et al. | |
| 2003/0065345 A1 | 4/2003 | Weadock | |
| 2003/0065346 A1 | 4/2003 | Evens et al. | |
| 2003/0083676 A1 | 5/2003 | Wallace | |
| 2003/0088256 A1 | 5/2003 | Conston et al. | |
| 2003/0105510 A1 | 6/2003 | DiMatteo et al. | |
| 2003/0114866 A1 | 6/2003 | Ulmsten et al. | |
| 2003/0120284 A1 | 6/2003 | Palacios | |
| 2003/0167064 A1 | 9/2003 | Whayne | |
| 2003/0181927 A1 | 9/2003 | Wallace | |
| 2003/0183671 A1 | 10/2003 | Mooradian et al. | |
| 2003/0208231 A1 | 11/2003 | Williamson, IV et al. | |
| 2004/0034377 A1 | 2/2004 | Sharkawy et al. | |
| 2004/0092960 A1 | 5/2004 | Abrams et al. | |
| 2004/0093029 A1 | 5/2004 | Zubik et al. | |
| 2004/0107006 A1 | 6/2004 | Francis et al. | |
| 2004/0116945 A1 | 6/2004 | Sharkawy et al. | |
| 2004/0142621 A1 | 7/2004 | Carroll et al. | |
| 2004/0172048 A1 | 9/2004 | Browning | |
| 2004/0209059 A1 | 10/2004 | Foss | |
| 2004/0215214 A1 | 10/2004 | Crews et al. | |
| 2004/0215219 A1 | 10/2004 | Eldridge et al. | |
| 2004/0215221 A1 | 10/2004 | Suyker et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021026 A1 | 1/2005 | Baily | |
| 2005/0021053 A1 | 1/2005 | Heinrich | |
| 2005/0021085 A1 | 1/2005 | Abrams et al. | |
| 2005/0059996 A1 | 3/2005 | Bauman et al. | |
| 2005/0059997 A1 * | 3/2005 | Bauman et al. | 606/219 |
| 2005/0070929 A1 | 3/2005 | Dalessandro et al. | |
| 2005/0118435 A1 | 6/2005 | Delucia et al. | |
| 2005/0228446 A1 | 10/2005 | Mooradian et al. | |
| 2005/0245965 A1 | 11/2005 | Orban et al. | |
| 2006/0004407 A1 | 1/2006 | Hiles et al. | |
| 2006/0135992 A1 | 6/2006 | Bettuchi et al. | |
| 2006/0173470 A1 | 8/2006 | Oray et al. | |
| 2006/0178683 A1 | 8/2006 | Shimoji et al. | |
| 2006/0212050 A1 | 9/2006 | D'Agostino et al. | |
| 2006/0271104 A1 | 11/2006 | Viola et al. | |
| 2007/0034669 A1 | 2/2007 | de la Torre et al. | |
| 2007/0049953 A2 | 3/2007 | Shimoji et al. | |
| 2007/0179528 A1 | 8/2007 | Soltz et al. | |
| 2007/0203509 A1 | 8/2007 | Bettuchi | |
| 2007/0203510 A1 | 8/2007 | Bettuchi | |
| 2007/0246505 A1 | 10/2007 | Pace-Floridia et al. | |
| 2008/0029570 A1 | 2/2008 | Shelton et al. | |
| 2008/0082126 A1 | 4/2008 | Murray et al. | |
| 2008/0110959 A1 | 5/2008 | Orban et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |

| | | | |
|---|---|---|---|
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban, III et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |

FOREIGN PATENT DOCUMENTS

| | | |
|---|---|---|
| DE | 19924311 A1 * | 11/2000 |
| EP | 0 594 148 | 4/1994 |
| EP | 0 327 022 | 4/1995 |
| EP | 0 667 119 | 8/1995 |
| EP | 1 064 883 | 1/2001 |
| EP | 1 759 640 | 3/2001 |
| EP | 1 256 317 | 11/2002 |
| EP | 1 520 525 | 4/2005 |
| EP | 1 621 141 | 2/2006 |
| EP | 1 994 890 A1 | 11/2008 |
| EP | 2 005 894 | 12/2008 |
| EP | 2 005 895 | 12/2008 |
| WO | WO90/05489 | 5/1990 |
| WO | WO 96/22055 A1 | 7/1996 |
| WO | WO97/01989 | 1/1997 |
| WO | WO97/13463 | 4/1997 |
| WO | WO98/17180 | 4/1998 |
| WO | WO99/45849 | 9/1999 |
| WO | WO03/082126 A1 | 10/2003 |
| WO | WO03/105698 A2 | 12/2003 |
| WO | WO2006/023578 | 3/2006 |
| WO | WO2006/044490 | 4/2006 |
| WO | WO 2006/083748 A1 | 8/2006 |
| WO | WO2006/083748 A1 | 8/2006 |
| WO | WO 2007/121579 A1 | 11/2007 |
| WO | WO2008/057281 | 5/2008 |
| WO | WO2008/109125 | 9/2008 |

OTHER PUBLICATIONS

International Search Report PCT/US/05/36740 dated Mar. 23, 2007.
International Search Report PCT/US2008/002981 dated Jun. 26, 2008.
European Search Report EP 08251779 dated Jul. 23, 2008.
European Search Report EP 05022585 dated Feb. 3, 2006.
European Search Report corresponding to EP 06004598 dated Jun. 22, 2006.
European Search Report corresponding to EP 08251989.3 dated Mar. 11, 2010 and mailed on Mar. 24, 2010.
European Search Report corresponding to EP 10250715.9 dated Jun. 30, 2010 and mailed on Jul. 20, 2010.
European Search Report corresponding to EP 05804382.9 dated Oct. 5, 2010 and mailed on Oct. 12, 2010.
European Search Report corresponding to EP 10251437.9 dated Nov. 22, 2010 and mailed on Dec. 16, 2010.
European Search Report corresponding to EP 09252897.5 dated Feb. 7, 2011 and mailed on Feb. 15, 2011.
European Search Report corresponding to EP 10250642.5 dated Mar. 25, 2011 and mailed on Apr. 4, 2011.
International Search Report corresponding to European Application No. EP 11 18 8309.6, completed on Dec. 15, 2011 and mailed on Jan. 12, 2012; 3 pages.

* cited by examiner

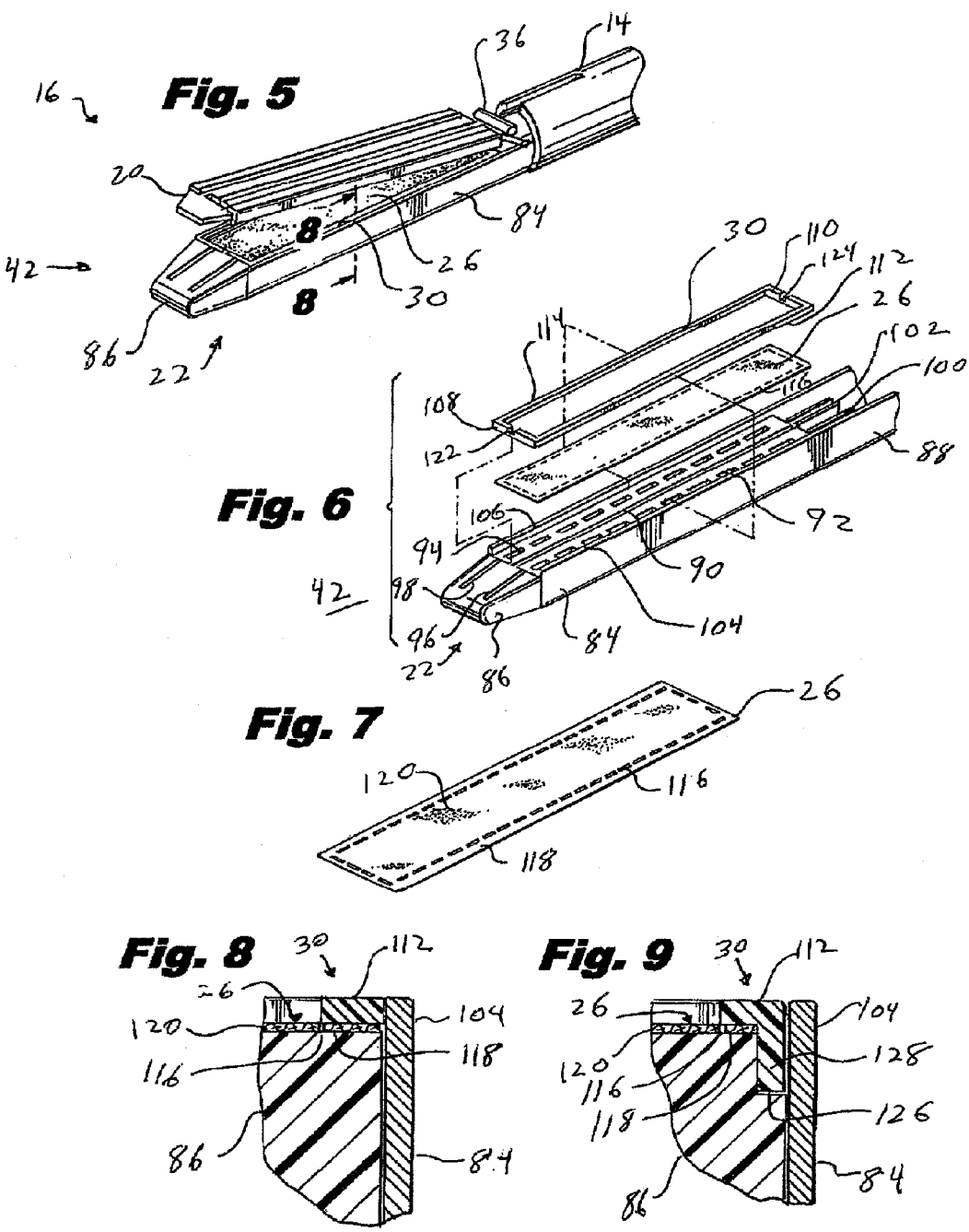

STAPLE BUTTRESS RETENTION SYSTEM

CROSS REFERENCE TO RELATED APPLICATIONS

The present application is a Continuation application which claims the benefit of and priority to U.S. patent application Ser. No. 12/984,891, filed on Jan. 5, 2011 now U.S Pat. No. 8,016,177, which is a Continuation application which claims the benefit of and priority to U.S. patent application Ser. No. 11/807,144, filed on May 25, 2007 now U.S. Pat. No. 8,038,045, the entire content of each of which is incorporated herein by reference.

BACKGROUND

1. Technical Field

The present disclosure relates to the application of buttress materials used in joining body tissue and attachment systems for attaching buttress materials to surgical instruments. More particularly, the present disclosure relates to systems and methods of temporarily attaching staple line buttress materials to the anvil and/or staple containing cartridge of a surgical stapling instrument.

2. Background of Related Art

Surgical stapling devices are employed by surgeons to sequentially or simultaneously apply one or more rows of fasteners, e.g., staples or two-part fasteners, to body tissue for the purpose of joining segments of body tissue together. Such devices generally consist of a pair of jaws or finger-like structures between which the body tissue to be joined is placed. When the stapling device is actuated, or "fired", a firing member or members contact staple drive members in one of the jaws. The staple drive members push the surgical staples through the body tissue and into an anvil in an opposite jaw which crimps the staples closed. If tissue is to be removed or separated, a knife blade can be provided in the jaws of the device to cut the tissue between the lines of staples.

When stapling relatively thin diseased, or fragile tissues, a buttress may be used to seal the staple line against air or fluid leakage. Additionally, a buttress may be used to reinforce the staple line against the tissue to prevent tears in the tissue or pulling of the staples through the tissue. A layer of buttress material is placed against the tissue and the tissue is stapled in conventional manner. It is known to position the buttress material on the stapling instrument itself prior to stapling the tissue. An exemplary example of this is disclosed in U.S. Pat. No. 5,542,594 to McKean et al. In McKean et al. the buttress material is slipped over the jaw of the stapler. The stapler is then actuated to staple the subject tissue and secure the buttress material between the tissue and staple line to reinforce the tissue and staple line.

It would be desirable to provide a system of attaching a limited amount of buttress material to a surgical instrument such that the material is localized on the jaws of the surgical instrument. It would also be desirable to provide a system of attaching buttress material to a surgical instrument that facilitates the release of the buttress material from the surgical instrument. Additionally, while the method disclosed in McKean is useful for open surgical procedures, it would be desirable to provide a system of attaching buttress material to the jaws of an endoscopic instrument. It would further be desirable to provide a system of attaching buttress material to the anvil and staple containing head of a circular surgical stapling instrument.

SUMMARY

There is disclosed a surgical instrument having a system of retaining buttress material. The surgical instrument includes a handle and an elongate member extending distally from the handle. A jaw assembly is mounted on the distal end of the elongate member and includes an anvil and a staple containing cartridge. A buttress retainer, having an open center, is positioned at least partially within the staple containing cartridge such that the buttress retainer frictionally engages the staple containing cartridge. The buttress material is positioned between the staple containing cartridge and the buttress retainer. The staple containing cartridge includes an outer channel having raised edges and a staple containing insert positioned within the outer channel. The buttress retainer frictionally engages the raised edges of the staple containing cartridge.

In one embodiment, the insert includes a side notch and the retainer includes a depending leg such that the depending leg sits in the side notch and frictionally engages the outer channel. In one embodiment the retainer is a circular ring for use with a circular surgical stapling instrument while in an alternative embodiment the retainer is rectangle for use with a linear surgical stapling instrument. In the alternative embodiment, at least one end of the retainer includes a notch configured to be cut by a blade of the surgical instrument.

In a particular embodiment, the buttress material includes a circumferential perforation line separating a central portion of the buttress material from a peripheral portion of the buttress material such that the central portion can be staple the tissue while the outer portion remains with the staple containing cartridge.

There is also disclosed the system of securing a buttress material to the anvil of a surgical instrument. A buttress retainer is configured to slide over the anvil such that the buttress retainer releasably retains at least a portion of the buttress material against the anvil. The buttress retainer includes a first rail and a second rail configured to be slid over the edges of the anvil. The first rail includes a first leg having a first inwardly directed lip configured to engage in edge of the anvil. In one embodiment, the first leg is flexible. The buttress retainer additionally includes an open center portion. In a specific embodiment, the buttress material includes a circumferential perforation line.

There is also disclosed an alternative system for securing a buttress material to the anvil of a surgical instrument. A buttress retainer is configured to engage the anvil in snap fit fashion such that the buttress retainer releasably retains the buttress material against the anvil. The buttress retainer includes at least one flexible leg having an inwardly directed projection configured to engage an edge of the anvil.

In one embodiment, the anvil is configured for use with a circular surgical stapling instrument. In this particular embodiment, the at least one flexible leg and inwardly directed projection are configured to engage a rim of an anvil cap of the anvil.

In an alternative embodiment, the anvil is configured for use with a linear surgical stapling instrument.

In a specific embodiment, buttress material includes a circumferential perforation line allowing a center portion of the buttress material to be stapled to tissue while the remainder of the buttress material remains with the anvil and buttress retainer.

DESCRIPTION OF THE DRAWINGS

Various embodiments of the presently disclosed systems for attaching staple line buttress materials to a surgical stapling instrument are disclosed herein with reference to the drawings, wherein:

FIG. 5 is a perspective view of the distal end of the surgical stapling instrument of FIG. 1;

FIG. 6 is a perspective view, with parts separated, of one embodiment of a staple cartridge and buttress material attachment system;

FIG. 7 is a perspective view of a sheet of buttress material configured for use with the system illustrated in FIG. 6;

FIG. 8 is a cross-sectional view taken along line 8-8 of FIG. 5 illustrating one embodiment of an attachment system;

FIG. 9 is a cross-sectional view similar to FIG. 8 illustrating an alternative embodiment of an attachment system;

DETAILED DESCRIPTION OF EMBODIMENTS

Embodiments of the presently disclosed buttress material attachment systems for use with surgical instruments will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
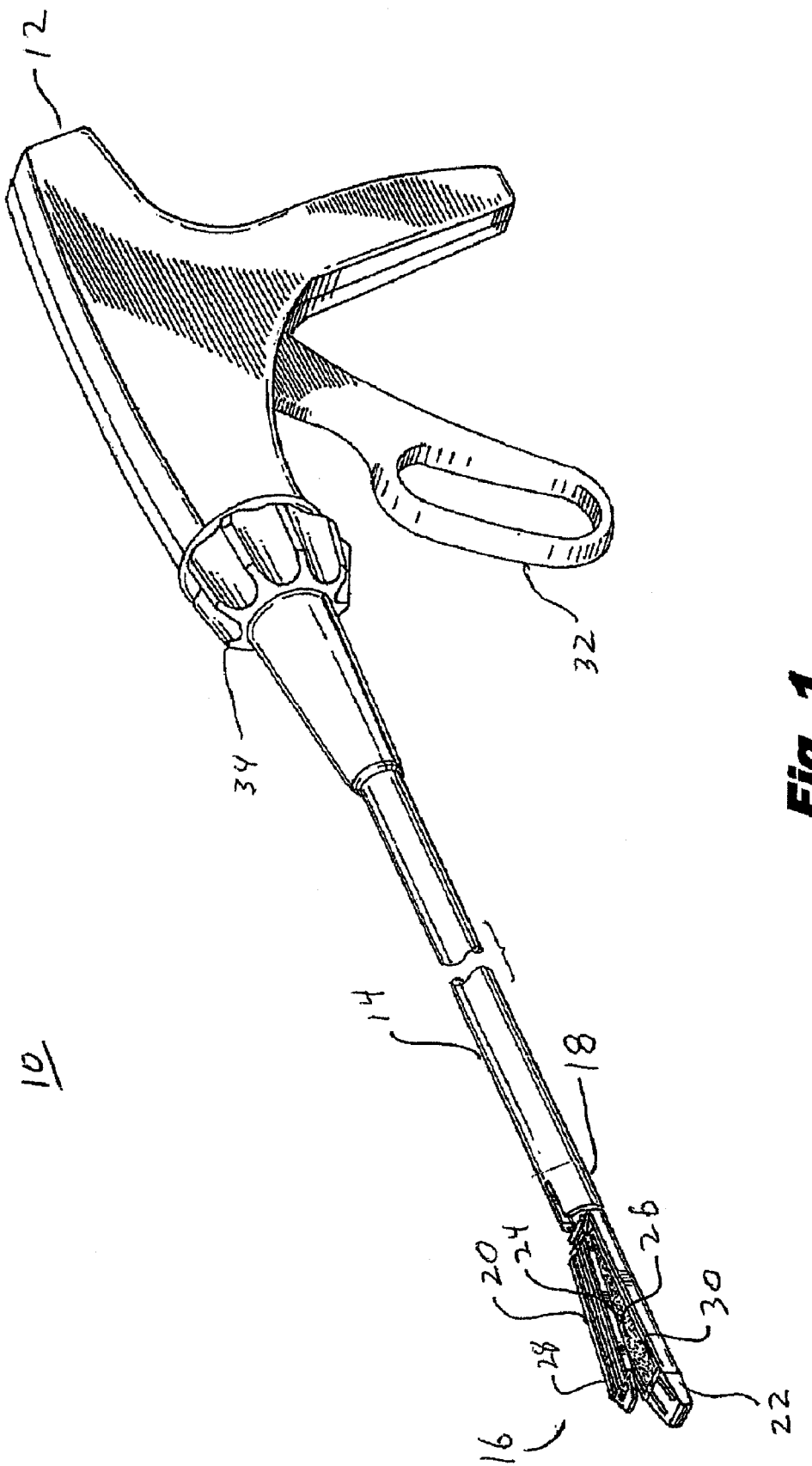
FIG. 1 is a perspective view of a surgical stapling instrument incorporating a system for attachment of staple line buttress materials.

Referring now to FIG. 1, there is disclosed a linear surgical stapling instrument or surgical stapler 10 for use in stapling tissue and applying layers of buttress material between the staples and underlying tissue. An example of this type of surgical stapling instrument is disclosed in U.S. Pat. No. 7,044,353, the entire disclosure of which is incorporated by reference herein. Surgical stapler 10 generally includes a handle 12 having an elongate tubular member 14 extending distally from handle 12. A jaw assembly 16 is mounted on a distal end 18 of elongate tubular member 14. Jaw assembly 16 includes a staple forming anvil 20 and a staple containing cartridge or staple cartridge 22. Staple cartridge 22 may be permanently affixed to elongate tubular member 14 or may be detachable and thus replaceable with a new staple cartridge 22. Staple clinching anvil 20 is movably mounted on distal end 18 of elongate tubular member 14 and is movable between an open position spaced apart from staple cartridge 22 to a closed position substantially adjacent staple cartridge 22.

Staple forming anvil 20 is provided with a layer of anvil buttress material 24 and staple cartridge 22 is provided with a layer of cartridge buttress material 26 in the manners described in more detail hereinbelow. The type of buttress material on the anvil 20 may be the same or different from the type of buttress material on the staple cartridge. An anvil buttress retainer 28 is provide to releasably secure anvil buttress material to staple forming anvil 20. Likewise, a cartridge buttress retainer 30 is provided to releasable secure cartridge buttress material 26 to staple cartridge 22. Anvil buttress material 24 and cartridge buttress material 26 are provided to reinforce, seal, and/or otherwise support staple lines applied to tissue by surgical stapler 10.

Surgical stapler 10 includes a trigger 32 movably mounted on handle 12. Actuation of trigger 32 initially operates to move anvil 20 from the open to the closed position relative to staple cartridge 22 and subsequently actuate surgical stapler 10 to apply lines of staples to tissue. In order to properly orient jaw assembly 16 relative to the tissue to be stapled, surgical stapler 10 is additionally provided with a rotation knob 34 mounted on handle 12. Rotation of rotation knob 34 relative to handle 12 rotates elongate tubular member 14 and jaw assembly 16 relative to handle 12 so as to properly orient jaw assembly 16 relative to the tissue to be stapled.

Figure 2:
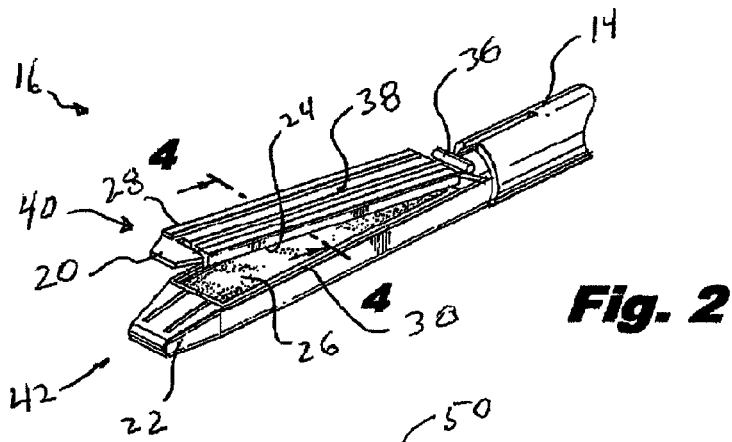
FIG. 2 is a perspective view of the distal end of the surgical stapling instrument of FIG. 1.

Referring to FIG. 2, a driver 36 is provided to move anvil 20 between the open and closed positions relative to staple cartridge 22. Driver 36 moves through a longitudinal slot 38 formed in anvil 20. A knife blade (not shown) is associated with driver 32 to cut tissue captured between anvil 20 and staple cartridge 22 as driver 36 passes through slot 38.

Anvil 20, anvil buttress material 24 and anvil buttress retainer 28 combine to form an anvil buttress attachment system 40 allowing anvil buttress material 24 to be supported on and releasably affixed to anvil 20. Similarly, staple cartridge 22, cartridge buttress material 26 and cartridge buttress retainer 30 combine to form a cartridge buttress attachment system 42 allowing cartridge buttress material 26 to be supported on and releasably affixed to staple cartridge 22. Anvil buttress attachment system 40 and cartridge buttress attachment system 42 are particularly configured to allow the respective buttress materials to be localized on inwardly facing surfaces of anvil 20 and staple cartridge 22 in order to facilitate passage of surgical stapler 10 into the body of a patient without risk of tearing or wrinkling of the respective buttress materials as surgical stapler 10 is inserted into and manipulated within the body of a patient.

Figure 3:
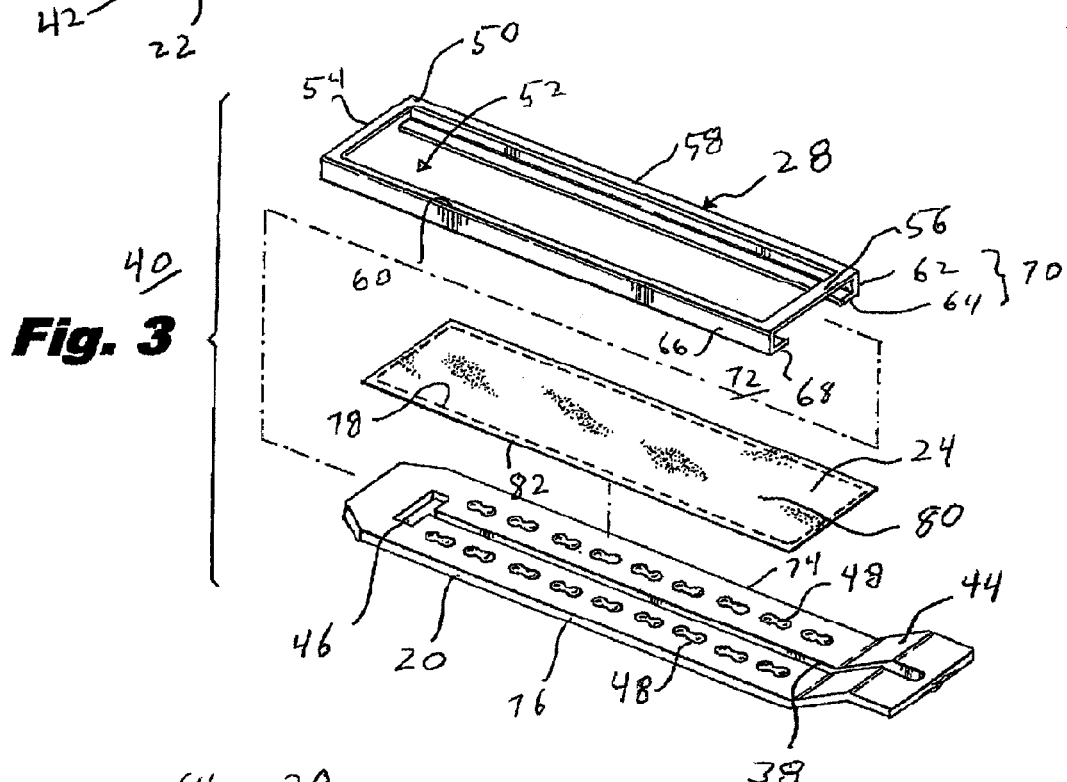
FIG. 3 is a perspective view, with parts separated, of an anvil and buttress material attachment system.

Referring to FIG. 3, in order to move anvil 20 between the open and closed positions, anvil 20 includes a proximal, angled or sloped edge 44 configured to be engaged by driver 36 in order to cam anvil 20 to the closed position. Slot 38 extends distally from sloped edge 44 and terminates in a transverse slot 46 which is configured to capture driver 36 upon complete actuation of surgical stapler 10 to prevent any further actuation of surgical stapler 10. In order to secure staples provided by staple cartridge 22 about the tissues and buttress materials, anvil 20 is provided with longitudinally extending rows of staple clinching pockets 48 located on either side of longitudinal slot 38. While only a single row of staple clinching pockets 48 is illustrated on either side of slot 38, it is contemplated that multiple and/or staggered rows of staple clinching pockets 48 may be provided on anvil 20.

Referring still to FIG. 3, anvil buttress attachment system 40, including anvil 20, anvil buttress material 24 and anvil buttress retainer 28 will now be described. The buttress material for the staple cartridge 22 and/or anvil 20 may be made from any biocompatible natural or synthetic material. The material from which the buttress material is formed may be bioabsorbable or non-bioabsorbable. It should of course be understood that any combination of natural, synthetic, bioabsorbable and non-bioabsorbable materials may be used to form the buttress material.

Some non-limiting examples of materials from which the buttress material may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the buttress material. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce the buttress material.

The buttress material may be porous or non-porous, or combinations of porous and non-porous layers. Where the buttress material is non-porous, buttress material may retard or prevent tissue ingrowth from surrounding tissues thereby acting as an adhesion barrier and preventing the formation of unwanted scar tissue. Thus, in embodiments, the buttress material possesses anti-adhesion properties. Techniques for forming non-porous layers from such materials are within the purview of those skilled in the art and include, for example, casting, molding and the like.

In embodiments, the buttress material is porous and possesses hemostatic properties. Where the buttress material is porous, it has openings or pores over at least a portion of a surface thereof. Suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

Where the buttress material is porous, the pores may be formed using any method suitable to forming a foam or sponge including, but not limited to the lyophilization or freeze-drying of a composition. Suitable techniques for making foams are within the purview of those skilled in the art. Porous buttress materials can be at least 0.2 cm thick, in embodiments from about 0.3 to about 1.5 cm thick. Porous buttress materials can have a density of not more than about 75 mg/cm$^2$ and, in embodiments below about 20 mg/cm$^2$. The size of the pores in the porous buttress materials can be from about 20 µm to about 300 µm, in embodiments from about 100 µm to about 200 µm.

The buttress material may also include a reinforcement member. The reinforcement member may be associated with a porous or non-porous layer or may be positioned between a non-porous layer and a porous layer of the buttress material. Alternatively, the reinforcement member may be positioned entirely within one or more of the individual layers (i.e., embedded within the porous layer, the non-porous layer, or both) of the buttress material. It is also envisioned that the reinforcement member may be positioned at the surface of one of the layers making up the buttress material and, in embodiments, may be positioned at an exterior surface of the buttress material.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material. As another example, the monofilaments or multifilament braids may be oriented in a common direction within the buttress material. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. In an illustrative embodiment, the buttress material has randomly oriented chopped fibers that have not been previously fused together embedded within in the buttress material.

It is envisioned that the reinforcement member may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to prevent adhesions from forming between the buttress material and the surrounding tissues opposite the target tissue. Some examples of these agents include, but are not limited to poly (vinyl pyrrolidone), carboxymethyl cellulose, hyaluronic acid, polyethylene oxide, poly vinyl alcohols and combinations thereof.

Suitable antimicrobial agents which may be included as a bioactive agent in the buttress material of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the buttress material in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Figure 4:
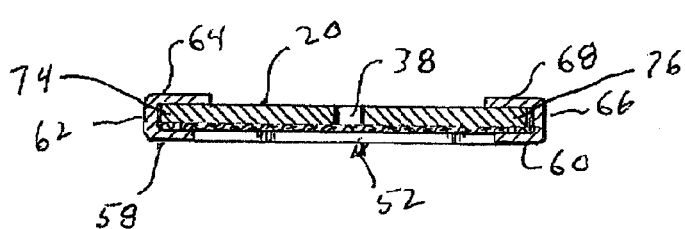
FIG. 4 is a cross-sectional view taken along line 4-4 of FIG. 2.

Referring still to FIG. 3, anvil buttress attachment system 40, including anvil 20, anvil buttress material 24 and anvil buttress retainer 28 will now be described. Referring to FIGS. 3 and 4, as shown, buttress retainer 28 is configured to releasably retain buttress material 24 against the face of anvil 20. Buttress retainer 28 is configured to slip or snap over anvil 20 to retain buttress material 24. Buttress retainer 28 includes a frame 50 defining a open center area 52 through which staples associated with staple cartridge 22 pass. Frame 50 includes a distal end 54 and a proximal end 56. First and second sides 58 and 60, respectively, extend between distal end 54 and proximal end 56. A first leg 62 depends from first side 58 and includes a first inwardly directed lip 64. Similarly, a second leg 66 depends from second side 60 and includes a second inwardly directed lip 68. First side 58, first leg 62 and first lip 64 form a first rail 70 for receipt of anvil 20 and second side 60, second leg 66 and second lip 68 form a second rail 72 for receipt of anvil 20.

Anvil buttress retainer 28 is affixed to anvil 20 by longitudinally sliding anvil buttress retainer 28 over anvil 20 such that first rail 70 slides over and frictionally engages a first side 74 of anvil 20 and second rail 72 slides over and frictionally engages a second side 76 of anvil 20 thereby trapping anvil buttress material between anvil buttress retainer 28 and anvil 20. Anvil buttress material 24 is exposed through open center 52 to staple cartridge 22. Anvil buttress material 24 is loosely retained between anvil buttress retainer 28 and anvil 20 such that, upon stapling anvil buttress material 24 to tissue, anvil buttress material 24 can pull free of anvil 20. First lip 64 and second lip 68 are sized to releasably retain the buttress material 24 and to allow the buttress material 24 to pull free of anvil 20 in use. Alternatively, anvil buttress material 24 can be firmly grasped between anvil 20 and anvil buttress retainer 28. In this embodiment, anvil buttress material 24 is formed with a circumferential perforation line 78 allowing a center portion 80 of anvil buttress material to pull apart from a peripheral portion 82 upon stapling center portion 80 to tissue. Peripheral portion 82 is captured and retained between anvil 20 and anvil buttress retainer 28.

In a further alternative embodiment, first and second legs 62 and 66 may be formed sufficiently flexible so as to snap fit over first and second sides 74 and 76, respectively, of anvil 20 as opposed to being longitudinally slid over anvil 20. Anvil buttress material 24 is then captured between anvil 20 and anvil buttress retainer 28 in any of the methods discussed hereinabove.

Referring to FIG. 5, and as noted hereinabove, jaw assembly 16 has cartridge buttress attachment system 42 including staple cartridge 22 and cartridge buttress material 30 secured to staple cartridge 22 by cartridge buttress retainer 30. Staple cartridge 22 is a known type of staple cartridge having a generally U-shaped outer channel 84 and a staple containing insert 86 positioned within outer channel 84. In a particular embodiment outer channel 84 is formed of stamped sheet metal while staple containing insert 86 is formed from a plastic material.

Referring now to FIG. 6, outer channel 84 includes a U-shaped proximal end 88 which allows staple cartridge 22 to be removably attached to elongate tubular member 14. Staple containing insert 86 includes a centrally located elongated slot 90 for passage of a knife associated with surgical stapler 10. Additionally, staple containing insert 86 includes longitudinally extending rows of staple containing pockets 92 and 94 positioned on either side of slot 90. Pockets 92 and 94 contain staples and staple pushers in a manner described in more detail hereinbelow. Further, staple containing insert includes longitudinally extending slots 96 and 98, positioned beneath rows of staple pockets 92 and 94, for receipt of staple drive members 100 and 102. Passage of staple drive members 100 and 102 beneath staple containing pockets 92 and 94 drive staples contained therein out of staple containing insert 86.

In order to secure cartridge buttress retainer 30 to staple containing cartridge 22, outer channel 84 includes first and second longitudinally extending raised edges 104 and 106 configured to capture cartridge buttress retainer 30 therebetween. Cartridge buttress retainer 30 includes a distal end 108 and a proximal end 110. First and second sides 112 and 114 extend between distal end 108 and proximal end 110. When cartridge buttress retainer 30 is assembled to staple containing cartridge 22, first side 112 frictionally engages first raised edge 104 while second side 114 frictionally engages second raised edge 106 thus firmly securing cartridge buttress retainer 30 between first and second raised edges 104 and 106 of outer channel 84 of staple containing cartridge 22.

Referring for the moment to FIG. 7, similar to staple buttress material 24 described hereinabove, cartridge buttress material 26 is provided with a circumferential perforation line 116 separating a peripheral portion 118 from a central portion 120 of cartridge buttress material 26.

Referring back to FIG. 6, in order for a knife blade (not shown), associated with surgical stapling instrument 10, to completely cut cartridge buttress material 26, distal end 108 of cartridge buttress retainer 30 is provided with a notch 122 and the cartridge buttress retainer 30 is configured at the notch 122 to be cut by the knife blade. Similarly, proximal end 110 is provided with a notch 124 and the cartridge buttress retainer 30 is configured at notch 124 to be cut by a knife blade during cutting of cartridge buttress material 26. The anvil buttress retainer 28 is similarly configured to be cut by the knife blade while remaining attached to anvil 20.

Referring now to FIG. 8, as discussed hereinabove, cartridge buttress material 26 is secured between cartridge buttress retainer 30 and staple containing insert 86 of staple cartridge 22. Specifically, peripheral portion 118 of cartridge buttress material 26 is trapped between first side 112 of cartridge buttress retainer 30 and staple containing insert 86. Central portion 120 of cartridge buttress material 26 is free to be stapled to tissue and separated from peripheral portion 118 along perforation line 116. As shown, first side 112 of cartridge buttress retainer 30 is frictionally retained by first raised edge 104 of outer channel 84. Alternatively, the perforation line 116 is omitted and the distal end 108, proximal end 110, first side 112 and/or second side 114 are sized to releasably retain buttress material 26 while allowing the buttress material 26 to slip through the open center area of the cartridge buttress retainer 30.

Referring for the moment to FIG. 9, an alternative method of securing cartridge buttress retainer 30 within staple cartridge 22 is illustrated. In this embodiment, staple containing insert 86 includes a side notch 126 which is configured to receive a depending leg 128 extending downwardly from first side 112 of cartridge buttress retainer 30. Specifically, depending leg 128 is captured between staple containing insert 86 and outer channel 84. Similar to the embodiment disclosed in FIG. 8, peripheral portion 118 of cartridge buttress material 26 is captured between first side 112 and staple containing insert 86. Central portion 120 is free to separate along perforation line 116 after being stapled to tissue.

Figure 10:
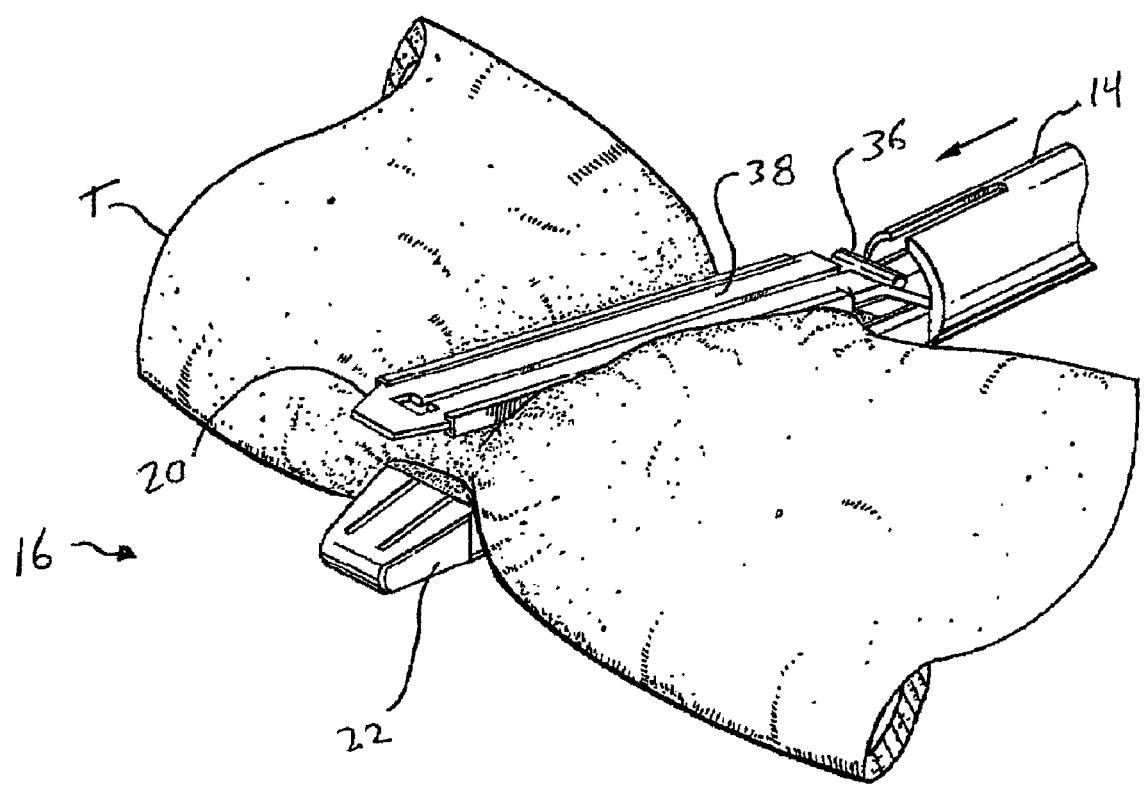
FIG. 10 is a perspective view of the distal end of the surgical stapling instrument in position on tubular tissue.
Figure 11:
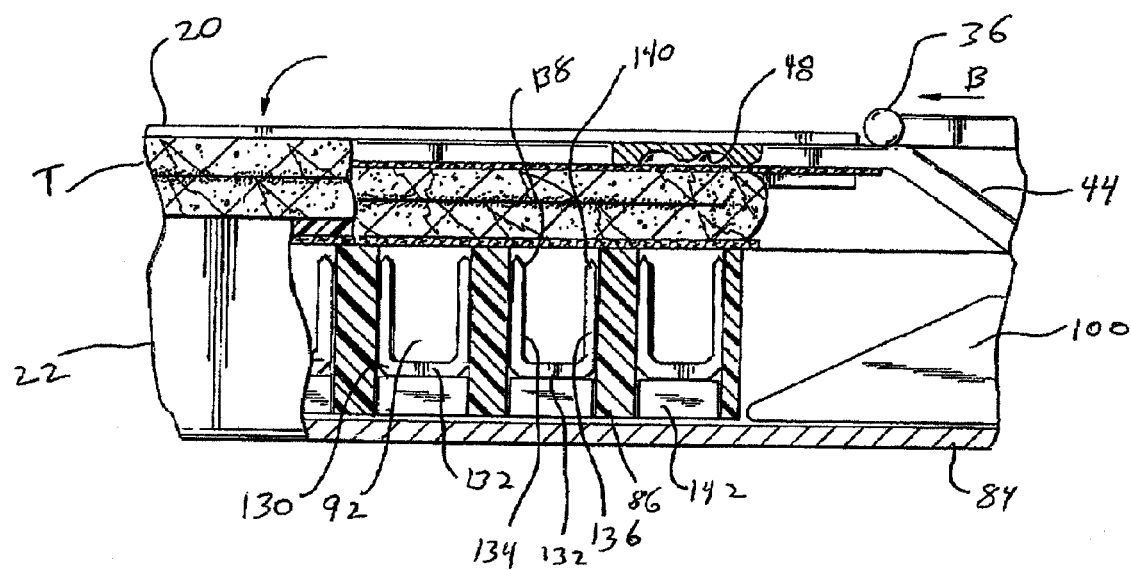
FIG. 11 is a cross-sectional view of a tissue section captured between an anvil and staple cartridge of the surgical instrument of FIG. 1.

Referring now to FIGS. 10 through 14, and initially with respect to FIGS. 10 and 11, the use of surgical stapler 10 to staple and divide a tubular tissue section T will now be described. Initially, jaw assembly 16, including anvil 20 and staple containing cartridge 22 are positioned around the tissue T to be stapled. Driver 36 is in a proximal position relative to slot 38. As best shown in FIG. 11, staple containing insert 86 includes staples 130 positioned within staple pockets 92. Staples 130 are of a conventional type and include a backspan 132 having a pair of legs 134 and 136 extending from backspan 132. Legs 134 and 136 terminate in tissue penetrating tips 138 and 140. Pushers 142 are located within staple pockets 92 and are positioned between staples 132 and the path of drive bar 100.

Figure 12:
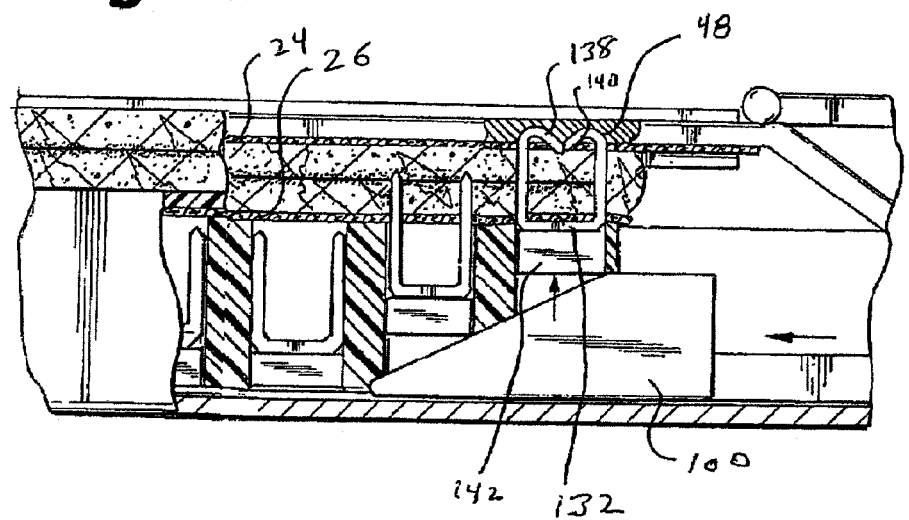
FIG. 12 is a cross-sectional view showing initial actuation of the surgical stapling instrument of FIG. 1.

Referring now to FIG. 11, surgical stapler 10 is initially actuated by movement of trigger 32 relative to handle 12 (FIG. 1) causing driver 36 to move in the direction of arrow B and against sloped edge 44 of anvil 20 thereby causing anvil 22 moved to the closed position relative to staple cartridge 22. As best shown in FIG. 12, as drive bar 100 advances distally within staple containing insert 86, drive bar 100 urges pushers 142 upwardly against backspans 132 of staples 130 driving staples in 30 through cartridge buttress material 26, tissue T, anvil buttress material 24 and towards staple forming pockets 48 in anvil 20. Tissue penetrating tips 138 and 140 are bent within staple clinching pockets 48 to thereby secure anvil buttress material 24 against tissue T while backspan 132 secures cartridge buttress material 26 against tissue T.

Figure 13:
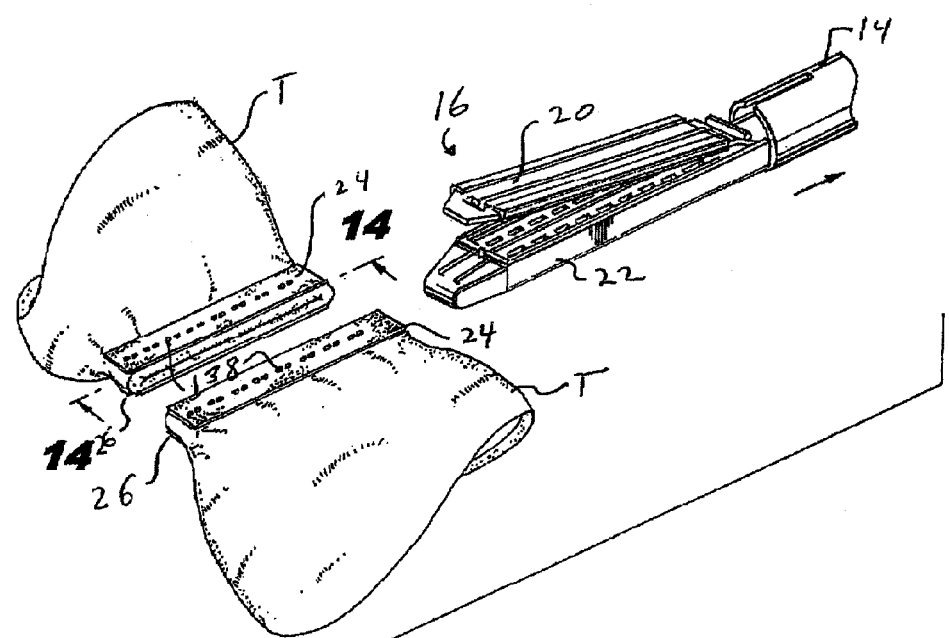
FIG. 13 is a perspective view of the distal end of the surgical stapling instrument and stapled tissue sections.

While not specifically shown, upon full actuation of surgical stapler 10, a knife blade associated with surgical stapler 10 and carried by driver 36 cuts tissue T, as well as anvil buttress material 24 and cartridge buttress material 26 between the rows of now formed staples 132. As shown in FIG. 13, in one embodiment, upon movement of anvil 22 to the open position, spaced apart from staple cartridge 22, anvil buttress material 24 pulls away from anvil 20 as described hereinabove. In an alternative embodiment, peripheral portion 82 of anvil buttress material 24 separates from central portion 80 along perforation line 78. Further, central portion 120 of cartridge buttress material 26 separates from peripheral portion 118 along perforation line 116 (FIG. 7) in the manner described hereinabove. Thus, peripheral portions 82 and 118 remain with anvil 20 and staple cartridge 22 as surgical stapler 10 is moved away from tissue T.

Figure 14:
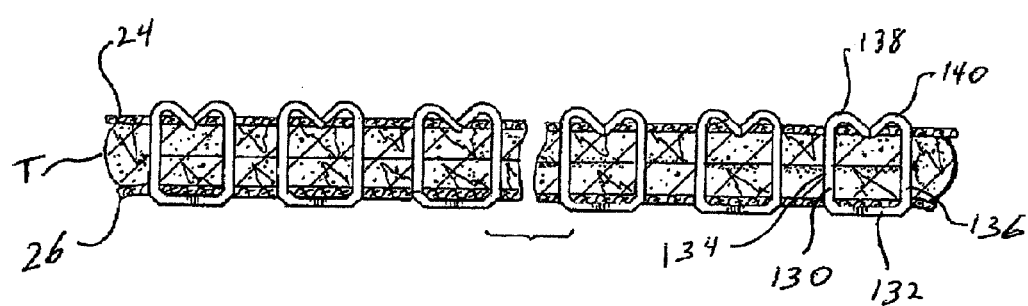
FIG. 14 is a cross-sectional view of the stapled tissue section taken along line 14-14 of FIG. 13.

The resulting tissue T stapled closed with staples 130 is best illustrated in FIG. 14. Specifically, cartridge buttress material 26 is secured against tissue T by backspans 132 of staples 130 and anvil buttress material 24 is secured against tissue T by the now formed tissue penetrating tips 138 and 140 of staples 130. In this manner, anvil buttress material 24 and cartridge buttress material 26 are stapled to tissue T thereby sealing and/or reinforcing these staple lines created by staples 130.

Figure 15:
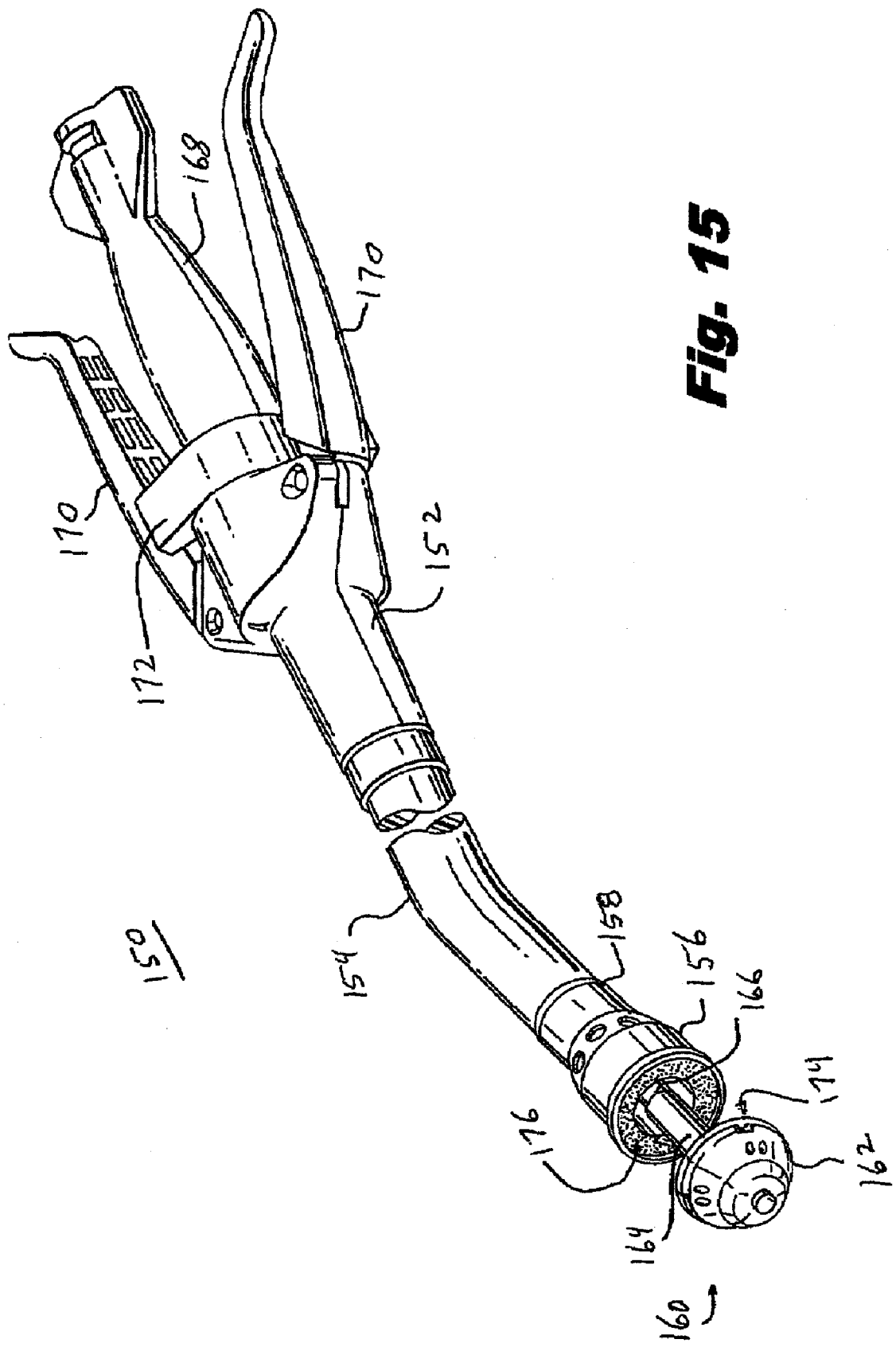
FIG. 15 is a perspective view of a circular stapling instrument in accordance with one embodiment of a buttress material attachment system.

Referring now to FIGS. 15-22, and initially with respect to FIG. 15, systems for releasably attaching buttress materials to a circular surgical stapler will now be described. Circular surgical stapler 150 is of known type generally including a handle 152 having an elongate member 154 extending distally from handle 152. A staple containing head or cartridge 156 is provided on a distal end of elongate member 154. Staple containing cartridge 156 houses staples (not shown) for insertion through tissue. Specifically, circular surgical stapler 150 is configured to apply one or more circular rows of staples to staple together two tubular tissue sections. An anvil 160 is provided to form the staples into a closed shape about tissue. Anvil 160 includes an anvil cap 162 having an anvil shaft 164 extending proximally from anvil cap 162. A shaft 166 extends from elongate member of 154 and is configured to releasably engage anvil shaft 164. An approximator 168 is rotatably mounted on handle 152 and is provided to approximate or move anvil 160 toward and away from staple containing cartridge 156.

A pair of arms 170 are pivotally mounted on handle 152 and are provided to actuate circular surgical stapler 150 so as to eject staples (not shown) out of staple containing cartridge 156. A lock 172 is provided on handle 152 to block and prevent actuation of circular surgical stapler 150 prior to anvil 160 being approximated adjacent staple containing cartridge 156. Circular surgical stapler 150 is provided with an anvil buttress material 174 releasably affixed to anvil cap 162 and a cartridge buttress material 176 provided on staple containing cartridge 156. Anvil buttress material 174 and cartridge buttress material 176 serve to reinforce and/or seal a staple line applied to tubular tissue sections by circular surgical stapler 150.

Figure 16:
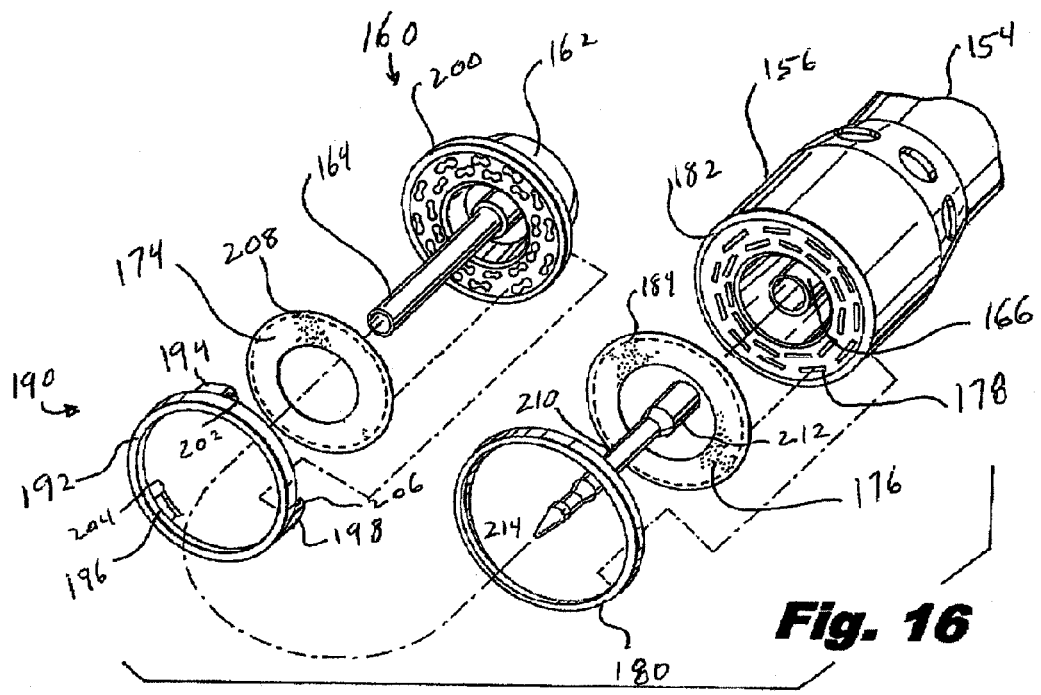
FIG. 16 is a perspective view, with parts separated, of the distal end of the circular surgical stapling instrument of FIG. 15.

Referring now to FIG. 16, staple containing cartridge 156 includes a plurality of staple pockets 178 containing staples as discussed in more detail below. Similar to that discussed hereinabove with respect to staple containing cartridge 22 of surgical stapler 10, in order to retain cartridge buttress material 176 on staple containing cartridge 156, circular surgical stapler is provided with a system including a circular ring or cartridge buttress retainer 180. Cartridge buttress retainer 180 is configured to frictionally engage a raised distal outer edge 182 formed on staple containing cartridge 156 thereby capturing cartridge buttress material 176 between cartridge buttress retainer 180 and staple containing cartridge 156. In one embodiment, cartridge buttress material 176 fits loosely between cartridge buttress retainer 180 and staple containing cartridge 156 such that, upon stapling to tissue, cartridge buttress material 176 is free to pull away from staple containing cartridge 156. In an alternative embodiment, cartridge buttress material 176 is provided with a circumferential perforation line 184 which allows a central portion of cartridge buttress material 176 to pull away from the remainder of the buttress material captured between staple containing cartridge 156 and cartridge buttress retainer 180.

Anvil 160 includes a plurality of circumferentially spaced staple forming pockets 186 formed in a face 188 of anvil cap 162 and configured to form the staples after they have been driven through tissue. Circular surgical stapler 150 is also provided with a system to retain anvil buttress material 174 against anvil 160. A circular ring or anvil buttress retainer 190 is provided having a circular frame 192 and a plurality of proximally facing legs or clips 194, 196 and 198 which are configured to engage a rim 200 of anvil cap 162. Specifically, clips 194, 196 and 198 are provided with inwardly projecting lips 202, 204 and 206 which are configured to engage rim 200 in a snap fit fashion. Similar to the system described hereinabove with respect to staple containing cartridge 156 and cartridge buttress material 176, in one embodiment, anvil buttress material 174 is free to pull out from between anvil buttress retainer 190 and anvil 160. In an alternative embodiment, anvil buttress material 174 is provided with a circumferential perforation line 208 which allows a center portion of anvil buttress material 174 to be staple to tissue while leaving an outer portion secured between anvil buttress retainer 190 and anvil 160.

As shown, in one embodiment, in order to secure anvil 160 to stapler 150, there is provided an adapter 210. A proximal end 212 of adapter 210 is configured to engage shaft 166 of circular surgical stapler 150. Adapter 210 includes a pointed distal end 214 configured to pierce tissue sections as well as engage anvil shaft 164.

Figure 17:
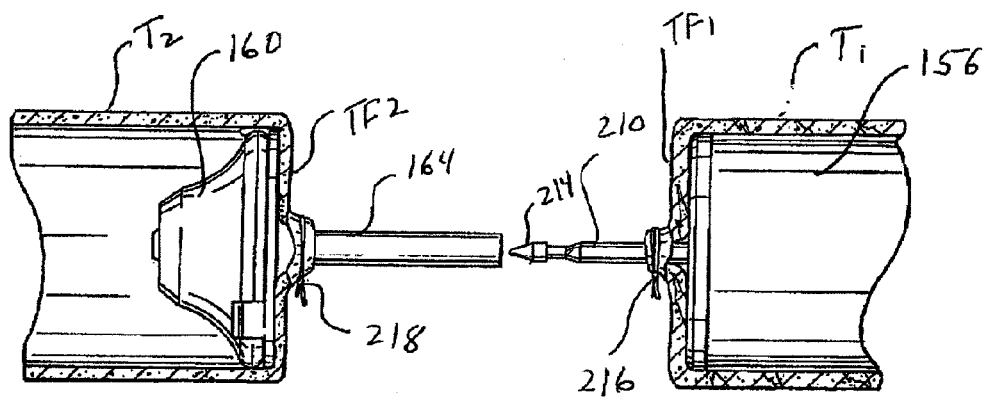
FIG. 17 is a side view, partially shown in section, of the distal end of the circular surgical stapling instrument of FIG. 15 positioned in a tubular tissue section.
Figure 18:
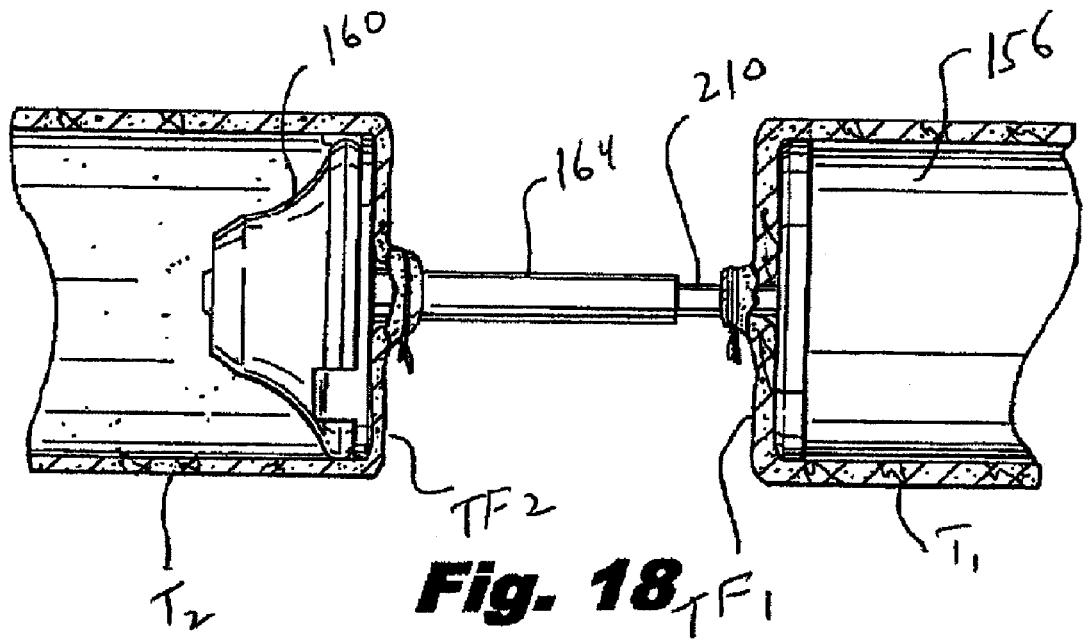
FIG. 18 is a side view illustrating the anvil of the circular surgical stapling instrument attached to the stapling containing head of the circular surgical stapling instrument.
Figure 19:
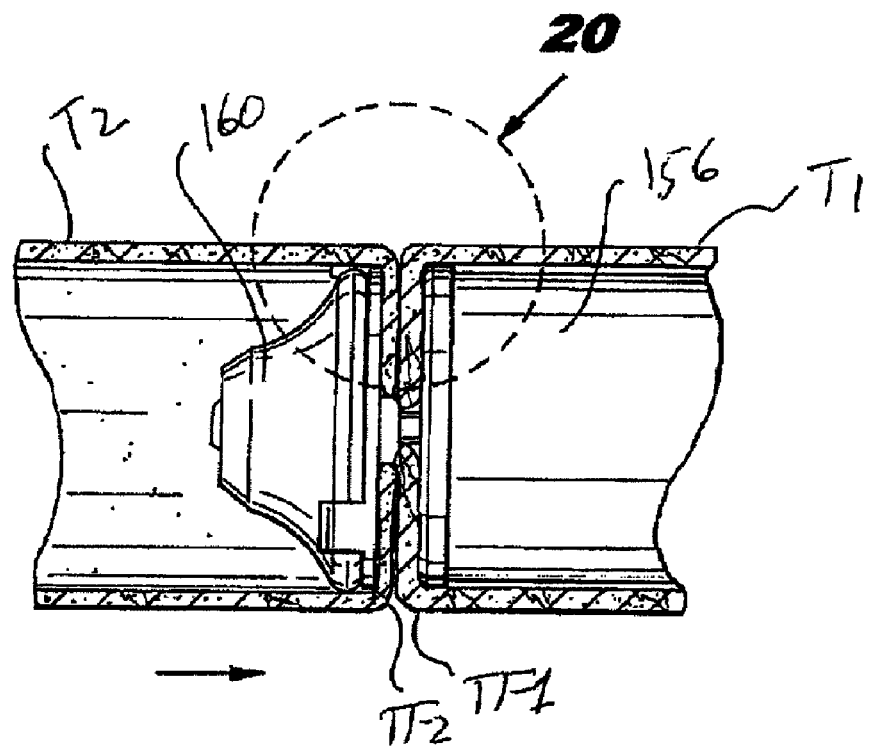
FIG. 19 is a side view showing the anvil and staple containing head approximated.

Referring now to FIGS. 15 and 17 to 22, and initially with regard to FIG. 17, the use of circular surgical stapler 150 to connect two tubular tissue sections and applied buttress material will now be described. Initially, staple containing cartridge 156 is positioned within a first tubular tissue section T1 such that adapted 210 extends beyond tissue T1. A purse string suture 216 is formed about tissue T1 and adapter 210 to form an inwardly directed tissue face TF1. Likewise, anvil 160 is positioned within a second tubular tissue section T2 such that anvil shaft 164 projects beyond tissue section T2 and is secured thereto by a second purse string suture 218 forming a second inwardly directed tissue face TF2. Adapter 210 is then inserted within anvil shaft 164 to connect staple containing cartridge 156 to anvil 160. (FIG. 18)

Once staple containing cartridge 156 has been connected to anvil 160, approximator 168 on handle 152 is rotated to draw anvil 160 toward staple containing cartridge 156 and thus bring first tissue face TF1 into flush engagement with the second tissue face TF2 and in a position to be stapled. (See FIGS. 1 and 19)

Figure 20:
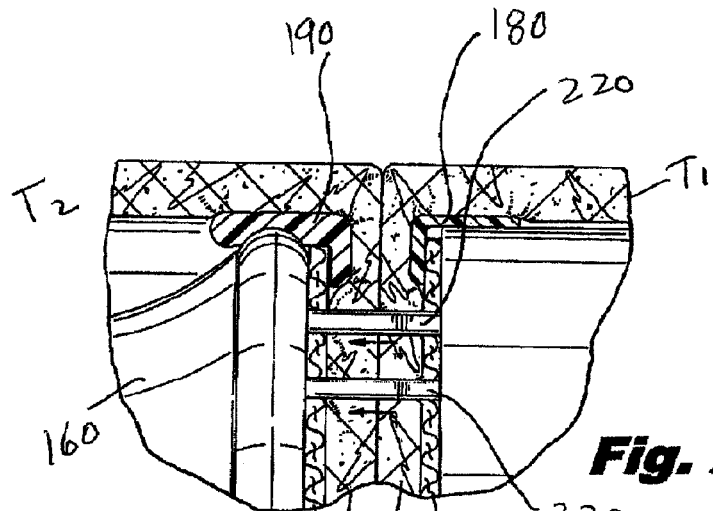
FIG. 20 is an enlarged area of detail view of FIG. 19.
Figure 21:
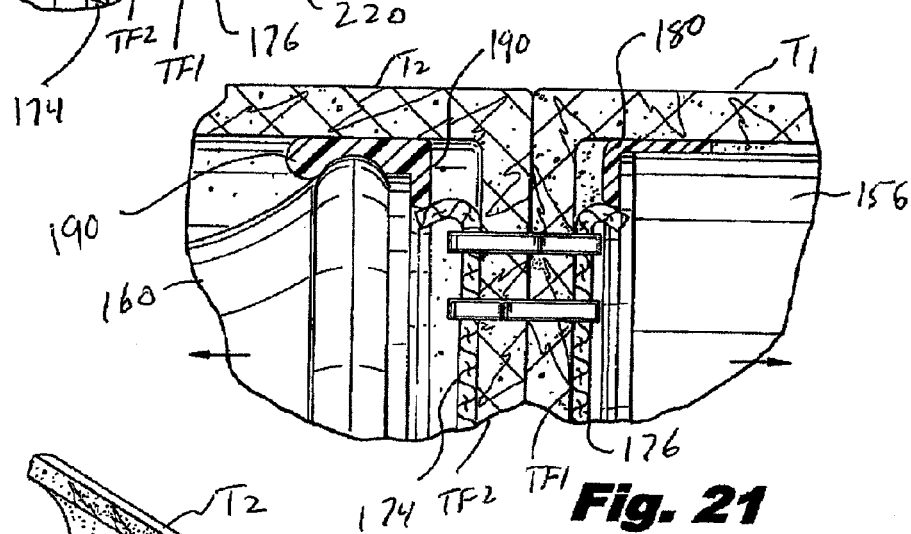
FIG. 21 is a detail view showing actuation of the circular surgical stapling instrument.

Referring to FIGS. 20 and 21, and as discussed hereinabove, staple containing cartridge 176 includes a plurality of staples 220. Circular surgical stapler 150 is actuated by releasing lock 172 and pivoting arms 170 (FIG. 1) thereby ejecting staples 220 out of staple containing cartridge 156 and through the tissue sections. Specifically, staples 220 pass through first tissue face TF1, cartridge buttress material 176, second tissue face TF2 and anvil buttress material 174. Staples to 20 are clinched closed about anvil buttress material 174 by staple clinching pockets 186 (FIG. 16)

As best shown in FIG. 21, once tissues T1 and T2 have been stapled together, anvil 160 is separated from staple containing cartridge 156. In one embodiment, cartridge buttress material 176 pulls free from cartridge buttress retainer 180 and anvil buttress material 174 pulls free from anvil buttress retainer 190. In an alternative embodiment, cartridge buttress material 176 separates along circumferential perforation line 184 and anvil buttress material 174 separates along circumferential perforation line 208.

Figure 22:
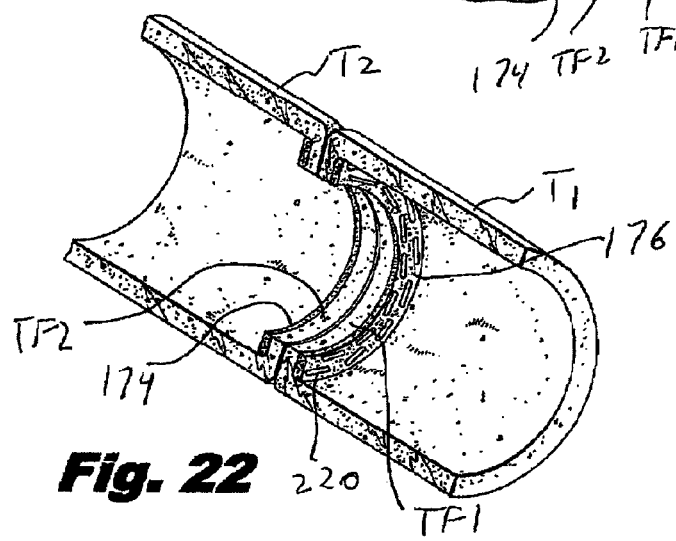
FIG. 22 is a perspective view, partially shown in section, of the stapled tubular tissue sections.

The resultant stapled tissue sections are clearly illustrated in FIG. 22. Once the tissue sections have been stapled, a circular knife (not shown) associated with circular surgical stapler 150 may be used to core out portions of the stapled tissue sections.

It should be noted that the disclosed attachment systems allow the buttress materials to be preloaded, i.e., positioned on the surgical stapler at the time of manufacture eliminating the need for installation in the operating room. Additionally, since the buttress materials are generally localized on the faces of the anvil and staple cartridge, the surgical stapler can be easily inserted through an access device without interference from the buttress material. The attachment systems include cartridge buttress retainers and/or anvil buttress retainers that slide onto a surgical instrument, snap onto the instrument, adhere to the instrument or frictionally engage the instrument, or any combination thereof. The instrument can include a retainer for the cartridge, anvil, or both.

It will be understood that various modifications may be made to the embodiments disclosed herein. For example, the disclosed buttress material retainer systems may be incorporated in open or endoscopic surgical stapling instruments. Further, the disclosed buttress material may include central, or otherwise located, perforation lines to facilitate separation of the buttress material from the associated anvil or staple containing cartridge. Additionally, the limited amount of adhesive may be used to temporarily secure the buttress material to the anvil or staple containing cartridge. Therefore, the above description should not be construed as limiting, but merely as exemplifications of particular embodiments. Those skilled in the art will envision other modifications within the scope and spirit of the claims appended hereto.

What is claimed is:

1. A surgical instrument having a system of retaining buttress material comprising:
   a jaw assembly including a first jaw and a second jaw, at least one of the first jaw and the second jaw defining staple pockets for retaining staples; and
   a buttress material having a central portion and a peripheral portion including a circumferential perforation line separating the central portion from the peripheral portion, the peripheral portion being attached to a tissue contacting surface of at least one of the first jaw and the second jaw, the central portion being separable from the peripheral portion after the staples are fired, the buttress material being preloaded on a surgical stapler at the time of manufacture.

2. The surgical instrument according to claim 1, further comprising a buttress retainer having an open center portion and being attached to at least one of the first jaw and the second jaw, the peripheral portion of the buttress material being retained against the tissue contacting surface of the at least one of the first jaw and the second jaw by the buttress retainer.

3. The surgical instrument according to claim 2, wherein the buttress retainer includes at least one depending leg for engaging at least one of the first jaw and the second jaw.

4. The surgical instrument according to claim 3, wherein the at least one depending leg of the buttress retainer includes an inwardly directed projection configured to engage an edge of one of the first jaw and the second jaw, to retain the edge of the corresponding jaw between the inwardly directed projection and the buttress retainer.

5. The surgical instrument according to claim 4, wherein the inwardly directed projection of the at least one depending leg of the buttress retainer is adapted to slide over the edge of the corresponding jaw.

6. The surgical instrument according to claim 4, wherein the inwardly directed projection of the at least one depending leg of the buttress retainer is adapted to snap fit over the edge of the corresponding jaw.

7. The surgical instrument according to claim 3, wherein the at least one depending leg frictionally engages the raised edge of the corresponding jaw.

8. The surgical instrument according to claim 7, wherein the at least one depending leg frictionally engages the raised edge of the corresponding jaw.

9. The surgical instrument according to claim 2, wherein the buttress retainer is a circular ring.

10. The surgical instrument according to claim 9, wherein the circular ring includes a plurality of depending legs for engaging at least one of the first jaw and the second jaw.

11. The surgical instrument according to claim 10, wherein the plurality of depending legs each includes an inwardly directed projection configured to engage an edge of one of the first jaw and the second jaw, to retain the edge of the corresponding jaw between the inwardly directed projection and the buttress retainer.

12. The surgical instrument according to claim 11, wherein the inwardly directed projections of the plurality of depending legs of the buttress retainer are adapted to snap fit over the edge of the corresponding jaw.

13. The surgical instrument of claim 10, wherein the plurality of depending legs extend in equidistant radial speed relation around the circular ring.

14. The surgical instrument according to claim 2, wherein the buttress retainer is a rectangular frame including a distal end and a proximal end, and a first side and a second side extending between the distal and proximal ends.

15. The surgical instrument according to claim 14, wherein the buttress retainer includes a first leg depending from the first side and a second leg depending from the second side.

16. The surgical instrument according to claim 15, wherein the first leg and the second leg extend longitudinally along an entire length of the corresponding side.

17. The surgical instrument according to claim 15, wherein the first leg and the second leg each include an inwardly directed projection configured to engage edges of one of the first jaw and the second jaw.

18. The surgical instrument according to claim 17, wherein the inwardly directed projections of the first and second legs of the buttress retainer are adapted to slide over the edges of the corresponding jaw.

19. The surgical instrument according to claim 17, wherein the inwardly directed projections of the first and second legs of the buttress retainer are adapted to snap fit over the edges of the corresponding jaw.

20. The surgical instrument according to claim 15, wherein the first leg and the second leg are configured to engage raised edges of one of the first jaw and second jaw.

21. The surgical instrument according to claim 20, wherein the first leg and the second leg frictionally engage the raised edges of the corresponding jaw.

22. The surgical instrument according to claim 1, wherein the first jaw and the second jaw each include a buttress material.

23. The surgical instrument according to claim 22, further comprising a first buttress retainer for retaining the buttress material of the first jaw and a second buttress retainer for retaining the buttress material of the second jaw, each of the first and second buttress retainers having an open center portion and being attached to its corresponding jaw, the peripheral portion of each buttress material being retained by its respective buttress retainer.

24. The surgical instrument according to claim 23, wherein the first buttress retainer is retained to the first jaw by engaging an edge of the first jaw and the second buttress retainer is retained to the second jaw by a friction fit against a raised edge of the second jaw.

25. The surgical instrument according to claim 22, wherein the buttress material of the first jaw is different from the buttress material of the second jaw.

26. The surgical instrument according to claim 1, wherein the buttress material is a constructed from a single material.

* * * * *

UNITED STATES PATENT AND TRADEMARK OFFICE
CERTIFICATE OF CORRECTION

| | | |
|---|---|---|
| PATENT NO. | : 8,210,414 B2 | Page 1 of 1 |
| APPLICATION NO. | : 13/205937 | |
| DATED | : July 3, 2012 | |
| INVENTOR(S) | : Michael Bettuchi | |

It is certified that error appears in the above-identified patent and that said Letters Patent is hereby corrected as shown below:

Title Page

In the section entitled "Related U.S. Application Data" should read:

(63) Continuation of application No. 12/984,891 filed on Jan. 5, 2011, now Pat. No. 8,016,177, which is a continuation of 11/807,144 filed on May 25, 2007, now Pat. No. 8,038,045.

Signed and Sealed this
Twenty-eighth Day of August, 2012

David J. Kappos
*Director of the United States Patent and Trademark Office*